US007915458B2

(12) United States Patent
Bruckmayer

(10) Patent No.: US 7,915,458 B2
(45) Date of Patent: Mar. 29, 2011

(54) METHOD OF AND DEVICE FOR INCREASING THE YIELD OF OIL PRODUCTION IN A PROCESS OF PRODUCING BIO-ETHANOL

(75) Inventor: Peter Bruckmayer, Velden-Eberspoint (DE)

(73) Assignee: Flottweg GmbH & Co. KGaA (DE)

( * ) Notice: Subject to any disclaimer, the term of this patent is extended or adjusted under 35 U.S.C. 154(b) by 1026 days.

(21) Appl. No.: 11/604,435

(22) Filed: Nov. 27, 2006

(65) Prior Publication Data

US 2008/0125612 A1 May 29, 2008

(51) Int. Cl.
*C07C 29/00* (2006.01)

(52) U.S. Cl. ........................................................ 568/840

(58) Field of Classification Search ................... 560/840
See application file for complete search history.

(56) References Cited

U.S. PATENT DOCUMENTS 5,795,477 A * 8/1998 Herman et al. ............ 210/360.1
2008/0110577 A1* 5/2008 Winsness .......................... 159/5

* cited by examiner

*Primary Examiner* — Deborah D Carr

(74) *Attorney, Agent, or Firm* — Gerald E. Hespos; Michael J. Porco

(57) ABSTRACT

A method of increasing the yield of oil production in a process of producing bio-ethanol in particularly comprises: creating concentrated syrup as a by-product from an ethanol production, and recovering oil from the concentrated syrup, wherein the step of recovering oil from the concentrated syrup includes using a horizontal axis centrifuge, and wherein the step of using a horizontal axis centrifuge includes using a bowl, a discharge of deoiled syrup and a baffle plate, the baffle plate being located inside of the bowl and retaining oil from the discharge of deoiled syrup.

20 Claims, 10 Drawing Sheets

METHOD OF AND DEVICE FOR INCREASING THE YIELD OF OIL PRODUCTION IN A PROCESS OF PRODUCING BIO-ETHANOL

BACKGROUND OF THE INVENTION

1. Field of the Invention

The present invention relates generally to a method of and a device for increasing the yield of oil production in a process of producing bio-ethanol.

2. Description of the Related Art

In known bio-ethanol plants stillage of grains such as corn is processed in order to produce ethyl alcohol, or so called bio-ethanol. The process usually is a dry milling process in which the starch in the grains is fermented. The fermentation creates a by-product or waste product, the so called whole stillage. The whole stillage is separated into distillers wet grains and the so called thin stillage. The thin stillage contains oil and is usually evaporated to become concentrated syrup and added to the solid waste materials to be dried and used as a supplement animal feed.

New efforts of improving this process are made by continuously pumping the concentrated syrup into a sedimentation tank and separating statically a part of the oil which is contained in the concentrated syrup. However, the yield of oil to be received in this new process is low.

Accordingly, a need exists for a method of and a device for increasing the yield of recovering oil in a process of producing bio-ethanol.

SUMMARY OF THE INVENTION

In accordance with one aspect of the invention, a method of increasing the yield of oil production in a process of producing bio-ethanol is disclosed, the method comprising: creating concentrated syrup as a by-product from an ethanol production, and recovering oil from the concentrated syrup, wherein the step of recovering oil from the concentrated syrup includes using a horizontal axis centrifuge, i.e., a centrifuge having a horizontal axis, and wherein the step of using a horizontal axis centrifuge includes using a bowl or drum, a discharge of deoiled syrup and a baffle plate or congestion plate, the baffle plate being located inside of the bowl and retaining oil from the discharge of deoiled syrup.

In accordance with another aspect of the invention, a device for increasing the yield of oil production in a process of producing bio-ethanol is disclosed, the device comprising: means for creating concentrated syrup as a by-product from an ethanol production, and means for recovering oil from the concentrated syrup, wherein said means for recovering oil from the concentrated syrup include a horizontal axis centrifuge, and wherein said horizontal axis centrifuge includes a bowl, a discharge of deoiled syrup and a baffle plate, the baffle plate being located inside of the bowl and retaining oil from the discharge of deoiled syrup.

In accordance with still another aspect of the invention, a method of increasing the yield of oil production in a process of producing bio-ethanol is disclosed, the method comprising: creating concentrated syrup as a by-product from an ethanol production, and recovering oil from the concentrated syrup, wherein the step of recovering oil from the concentrated syrup includes using a horizontal axis centrifuge, and wherein the step of using a horizontal axis centrifuge includes using a discharge of oil at a bowl of the horizontal axis centrifuge, the discharge diameter of which is 0.90 to 1.10 times of the respective diameter of a discharge of deoiled syrup.

In accordance with yet another aspect of the invention, a device for increasing the yield of oil production in a process of producing bio-ethanol is disclosed, the device comprising: means for creating concentrated syrup as a by-product from an ethanol production, and means for recovering oil from the concentrated syrup, wherein said means for recovering oil from the concentrated syrup include a horizontal axis centrifuge, and wherein said horizontal axis centrifuge includes a bowl, and a discharge of deoiled syrup and a discharge of oil at said bowl, the discharge diameter of said discharge of oil being 0.90 to 1.10 times of the respective diameter of said discharge of deoiled syrup.

In accordance with still a further aspect of the invention, a method of increasing the yield of oil production in a process of producing bio-ethanol is provided, the method comprising: creating concentrated syrup as a by-product from an ethanol production, and recovering oil from the concentrated syrup, wherein the step of recovering oil from the concentrated syrup includes using a horizontal axis centrifuge, and wherein the step of using a horizontal axis centrifuge includes using a three-phase horizontal axis centrifuge.

In accordance with yet another aspect of the invention, a device for increasing the yield of oil production in a process of producing bio-ethanol is disclosed, the device comprising: means for creating concentrated syrup as a by-product from an ethanol production, and means for recovering oil from the concentrated syrup, wherein said means for recovering oil from the concentrated syrup include a horizontal axis centrifuge, and wherein said horizontal axis centrifuge is a three-phase horizontal axis centrifuge.

Preferably the step of using a baffle plate inside of a bowl of the horizontal axis centrifuge includes using a baffle plate, the diameter of which is 0.70 to 0.95 times of the respective diameter of the bowl of the horizontal axis centrifuge.

In a preferred embodiment, the step of using a horizontal axis centrifuge includes discharging the recovered oil from the horizontal axis centrifuge by using an adjustable weir disk.

In another preferred embodiment, the step of using a horizontal axis centrifuge includes discharging the recovered oil from the horizontal axis centrifuge by using an impeller disk or peeling disk.

Further preferred, the step of creating concentrated syrup as a by-product from an ethanol production includes producing whole stillage, recovering thin stillage from the whole syrup by using a horizontal axis centrifuge and concentrating the thin stillage by using an evaporator.

In a further preferred embodiment, the step of recovering oil from the concentrated syrup includes storing the concentrated syrup in a storage tank before conducting it to the horizontal axis centrifuge.

The step of conducting the concentrated syrup from the storage tank to the horizontal axis centrifuge further preferably includes drawing off the concentrated syrup at the top of the syrup stored in the storage tank.

Finally, in a further preferred embodiment the step of using a horizontal axis centrifuge includes providing a centrifugal acceleration of 1800 to 2100×G, preferably 1900 to 2000×G, most preferred 1960×G on the concentrated syrup in the horizontal axis centrifuge.

DETAILED DESCRIPTION OF THE PREFERRED EMBODIMENTS

Figure 1:
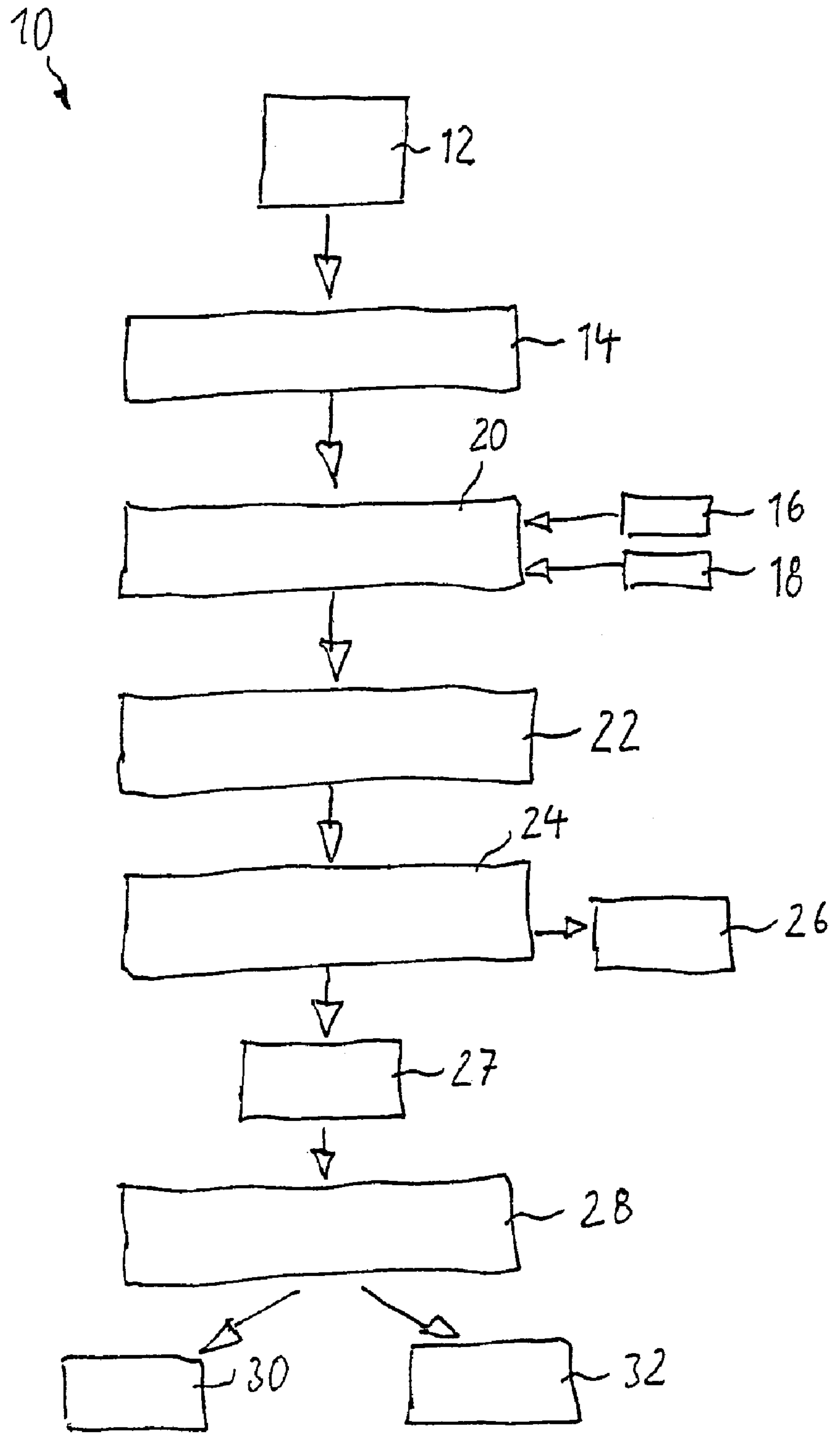
FIG. 1 is a schematic flow chart illustrating the process of producing bio-ethanol and creating whole stillage as a by-product of said production of bio-ethanol.

In FIG. 1 a method 10 of producing bio-ethanol is shown. In a first step of this method 10, grain 12 such as corn, is provided and milled in a step 14. After said milling, water 16 and enzymes 18 are added. By heating of the mixture a liquefaction of starch is started and the enzymes provide a decomposition of starch into sugar in a step 20. A further fermentation takes place in a step 22 converting the sugar into ethanol.

The step 22 is followed by a distillation step 24 in which bio-ethanol 26 is received. The by-product of the distillation step 24, a so called whole stillage 27, is further separated mechanically in a step 28 via a horizontal axis centrifuge, preferable a two-phase helical conveyor centrifuge. In said step 28 the whole stillage 27 is separated into a solid phase, the so called distillers wet grains 30, and a liquid phase, the so called thin stillage 32.

Figure 2:
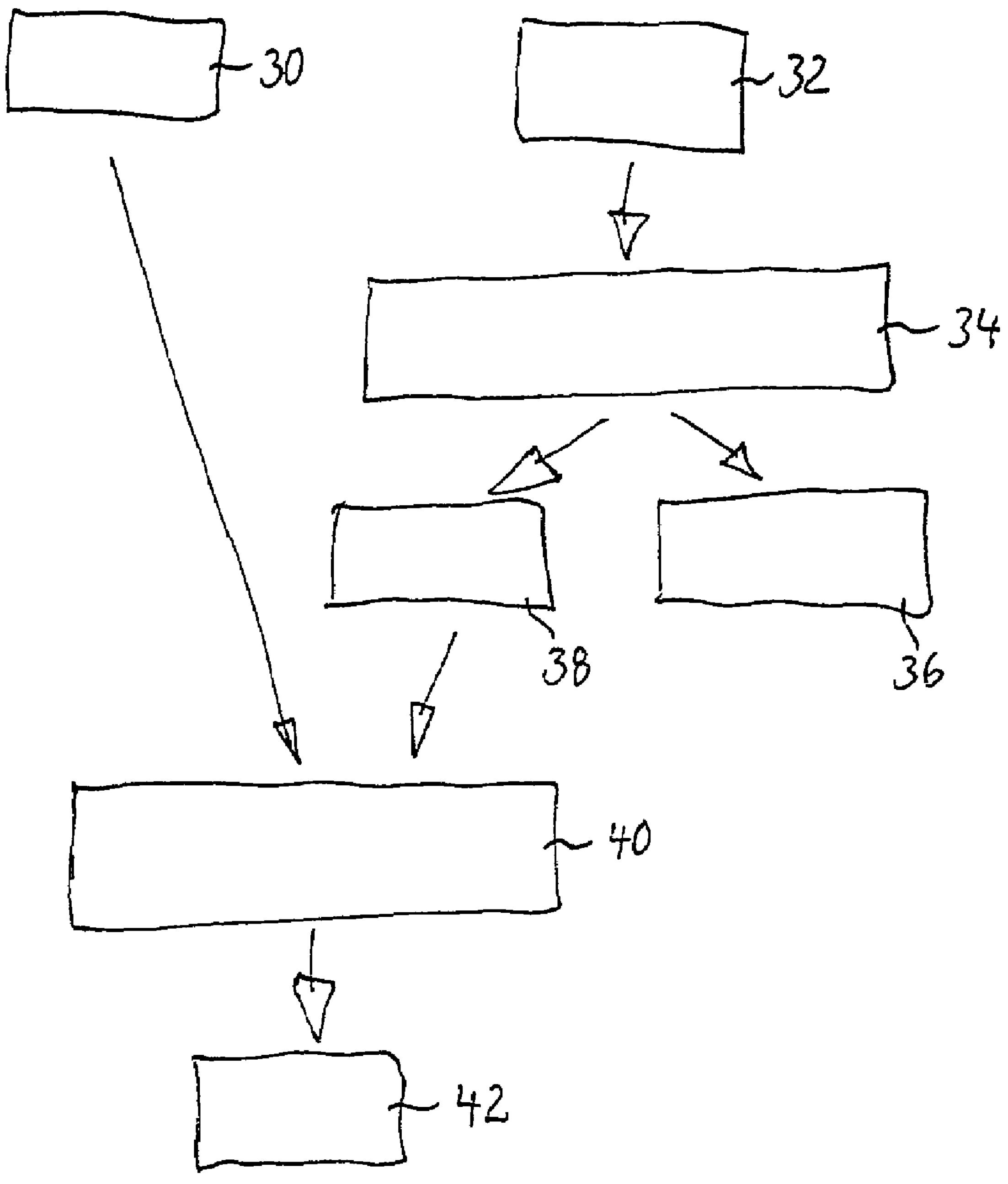
FIG. 2 is a schematic flow chart illustrating the processing of the whole stillage of the bio-ethanol production of FIG. 1 according to the prior art.

In FIG. 2 the further processing of the distillers wet grains 30 and the thin stillage 32 according to the prior art is depicted. The thin stillage 32 is conducted to an evaporation step 34 in which water 36 is removed from a so called syrup 38. The syrup 38 is added to the distillers wet grains 30 and dried in a step 40 in order to receive so called distillers dried grains with solubles 42. The distillers dried grains with solubles 42 is used as a supplement animal feed.

Figure 3:
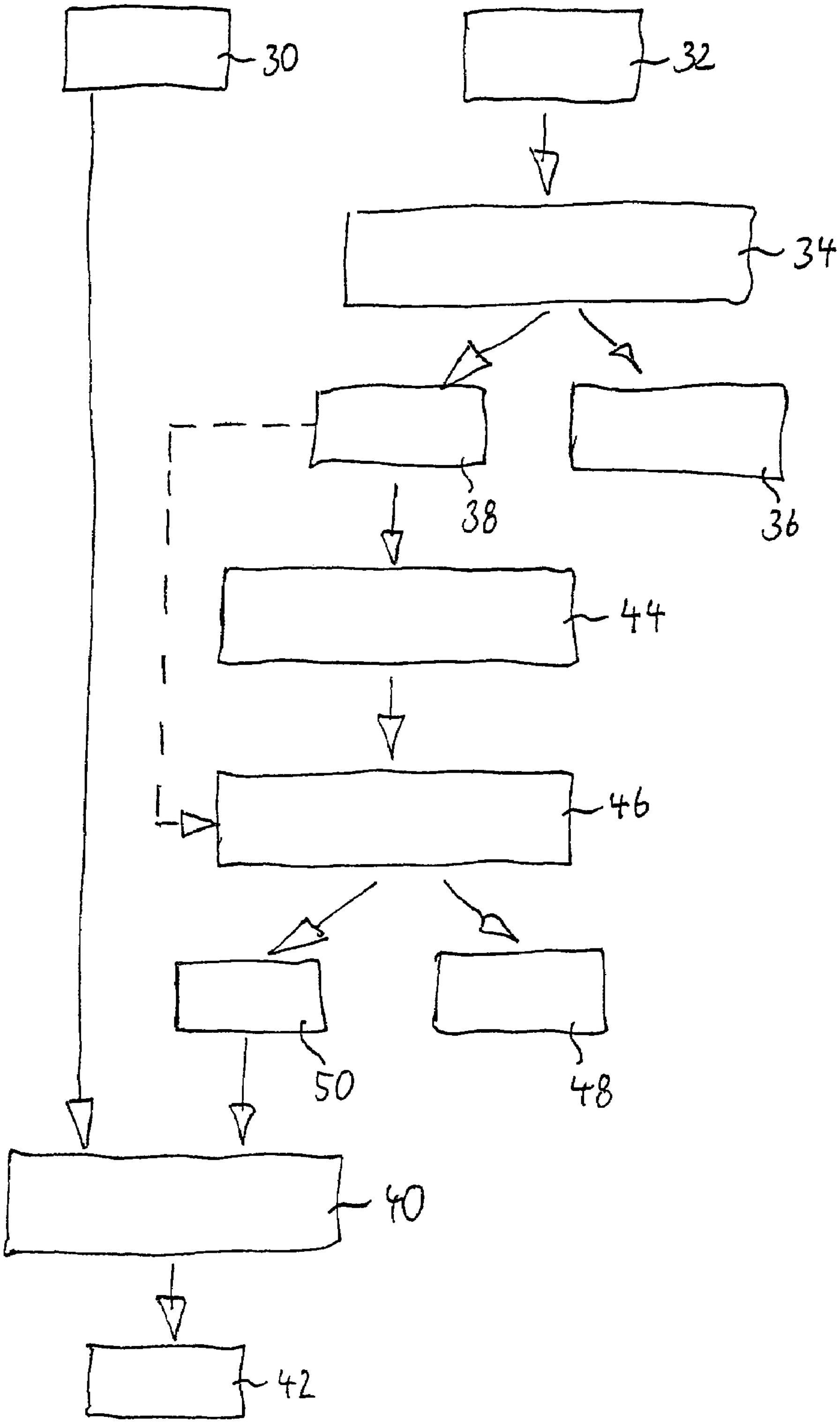
FIG. 3 is a schematic flow chart illustrating the processing of the whole stillage of the bio-ethanol production of FIG. 1 according to the invention, in order to increase the yield of oil production in the production of bio-ethanol.

In FIG. 3 the further processing of the thin stillage 32 according to the invention is depicted. The process according to the invention differs from the one of FIG. 2 in that the syrup 38 is conducted to a sedimentation or storage tank 44 and further to a horizontal axis centrifuge 46. The line for conducting the syrup 38 from the storage tank 44 to the horizontal axis centrifuge 46 is advantageously connected to the storage tank 44 above the feed of the storage tank 44. Alternatively, the line is connected to the bottom of the storage tank 44. Further preferred, the syrup 38 is conducted directly to the horizontal axis centrifuge 46. The horizontal axis centrifuge 46 is especially adapted to recover a large amount of oil 48 out of the syrup 38 for improving the yield of recovering oil in said process 10 of producing bio-ethanol 26.

The rest of the syrup 38, a so called deoiled syrup 50, is conducted to the above mentioned step 40 in which it is dried, in order to become distillers dried grains with solubles 42.

Figure 4:
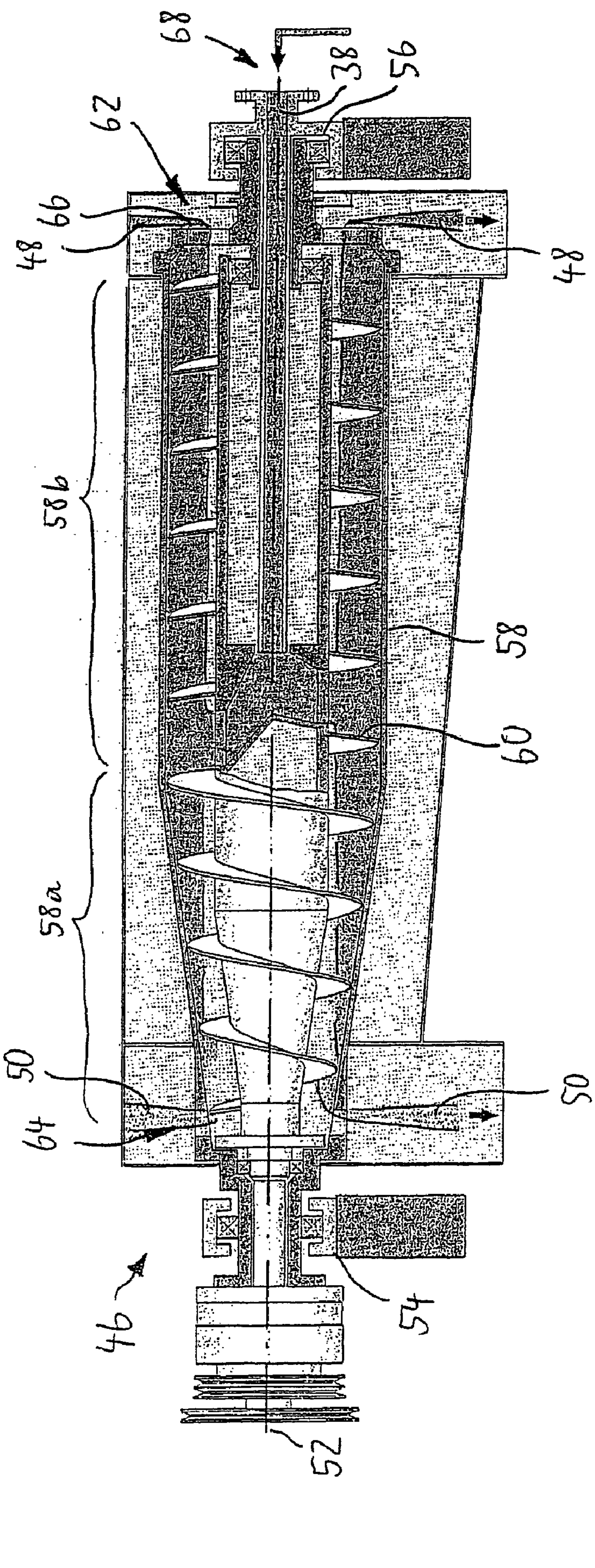
FIG. 4 is a longitudinal sectional view of a first embodiment of a device for increasing the yield of oil production in the process of producing bio-ethanol according to the invention.

FIG. 4 shows a first embodiment of a horizontal axis centrifuge 46 which is used in the process of FIG. 3 for recovering oil 48 from the concentrated syrup 38. The horizontal axis centrifuge 46 includes a horizontal rotation axis 52 and two bearings 54 and 56 on which a bowl or bowl 58 having a rotatable screw 60 therein is supported rotationally with respect to the axis 52. The horizontal axis centrifuge 46 provides a centrifugal acceleration of 1800 to 2100×G, preferably 1900 to 2000×G, most preferred 1960×G on syrup 38, which is located in the horizontal axis centrifuge 46.

The bowl 58 is provided with a first outlet 62 for a "liquid phase" and a second outlet 64 for a "solid phase". The first outlet 62 is provided with an adjustable weir disk or plate 66 at one of the front walls of the bowl 58, and the second outlet 64 is provided at the opposite front wall of the bowl 58 at a conical part 58*a* thereof. The conical part 58*a* forms nearly one half of the outer wall of the bowl 58. The screw 60 serves as a transportation means in order to discharge material from a cylindrical part 58*b* of the bowl 58 radial inwardly along the conical part 58*a* and out of the second outlet 64.

The syrup 38 to be separated in the horizontal axis centrifuge 46 is conducted into the bowl 58 through an inlet 68 in the centre of the screw 60. The recovered oil 48 is discharged via the first outlet 62 across the adjustable weir disk 66, which may be adjusted even during rotation of bowl 58 and screw 60. The deoiled syrup 50 is discharged via the screw 60 along said conical part 58*a* through the second outlet 64.

Figure 5:
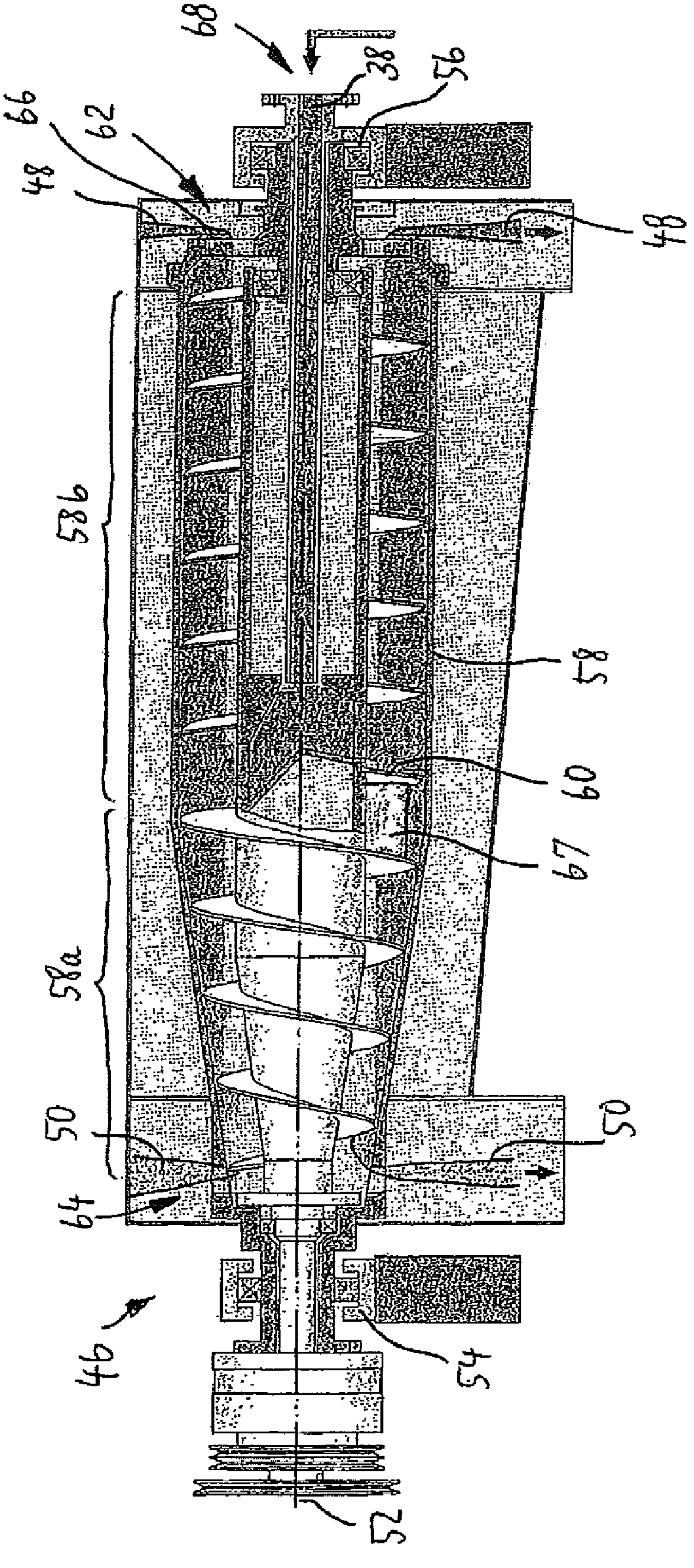
FIG. 5 is a longitudinal sectional view of a device similar to FIG. 4 modified according to the invention.

In order to further improve the process of discharging the deoiled syrup 50 relative to the recovered oil 48, a modified horizontal axis centrifuge 46 is depicted in FIG. 5, which is similar to the one of FIG. 4 except of a baffle plate 67 being located in one of the windings of screw 60 at the transition of the cylindrical part 58*b* to the conical part 58*a* of the bowl 58. The baffle plate 67 serves to retain oil 48 from the second outlet 64, said oil 48 floating on the syrup 38 in the radial inner part of bowl 58. The baffle plate 67 is located at the screw 60 alternatively at the transition between the cylindrical part and the conical part of its windings. The baffle plate 67 begins at the hub of the screw 60 and is directed radial outwardly. It should be directed approximately lengthwise, i.e., in one of the planes in which the horizontal rotation axis 52 is located (see FIG. 5). Alternatively, the baffle plate 67 may be directed orthogonal to the horizontal rotation axis 52.

The baffle plate 67 further helps to transport the deoiled syrup to the second discharge 64. The deoiled syrup is very soft or pasty. Thus, the deoiled syrup is transported as a "heavy phase" via an accumulation at the baffle plate 67. In other words, the deoiled syrup is pressed under the baffle plate 67 and up the conical part 58*a*. In order to improve said transport of deoiled syrup, the diameter of the baffle plate 67 is 0.70 to 0.95 times of the respective diameter of the bowl 58.

Figure 6:
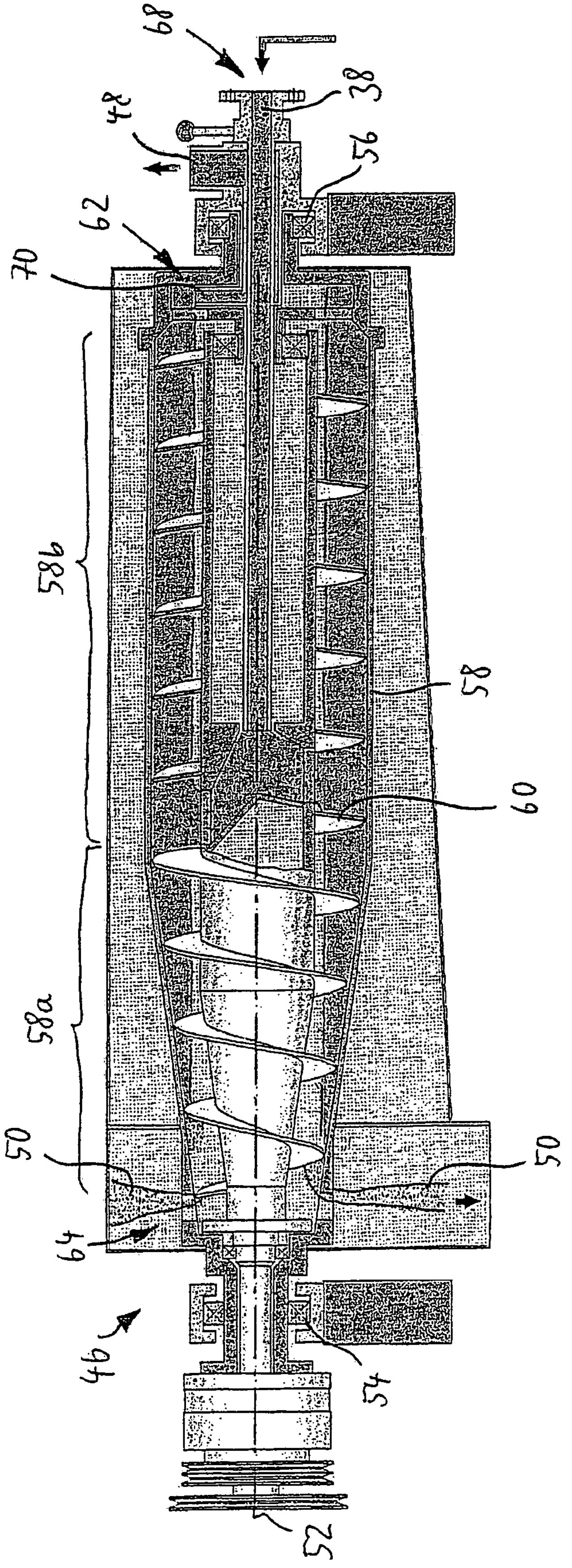
FIG. 6 is a longitudinal sectional view of a second embodiment of a device for increasing the yield of oil production in the process of producing bio-ethanol according to the invention.

In FIG. 6 a second embodiment of a horizontal axis centrifuge 46 for recovering oil 48 from the concentrated syrup 38 according to the process of FIG. 3 is shown. The horizontal axis centrifuge 46 of FIG. 6 also includes a horizontal rotation axis 52 and two bearings 54 and 56 on which a rotatable drum or bowl 58 having a rotatable screw 60 therein is supported. The bowl 58 is again provided with a first outlet 62 for a "liquid phase" and a second outlet 64 for a "solid phase". The first outlet 62 is provided with an impeller disk 70 at a front wall of the bowl 58 which is opposite of a conical part 58*a*.

Figure 7:
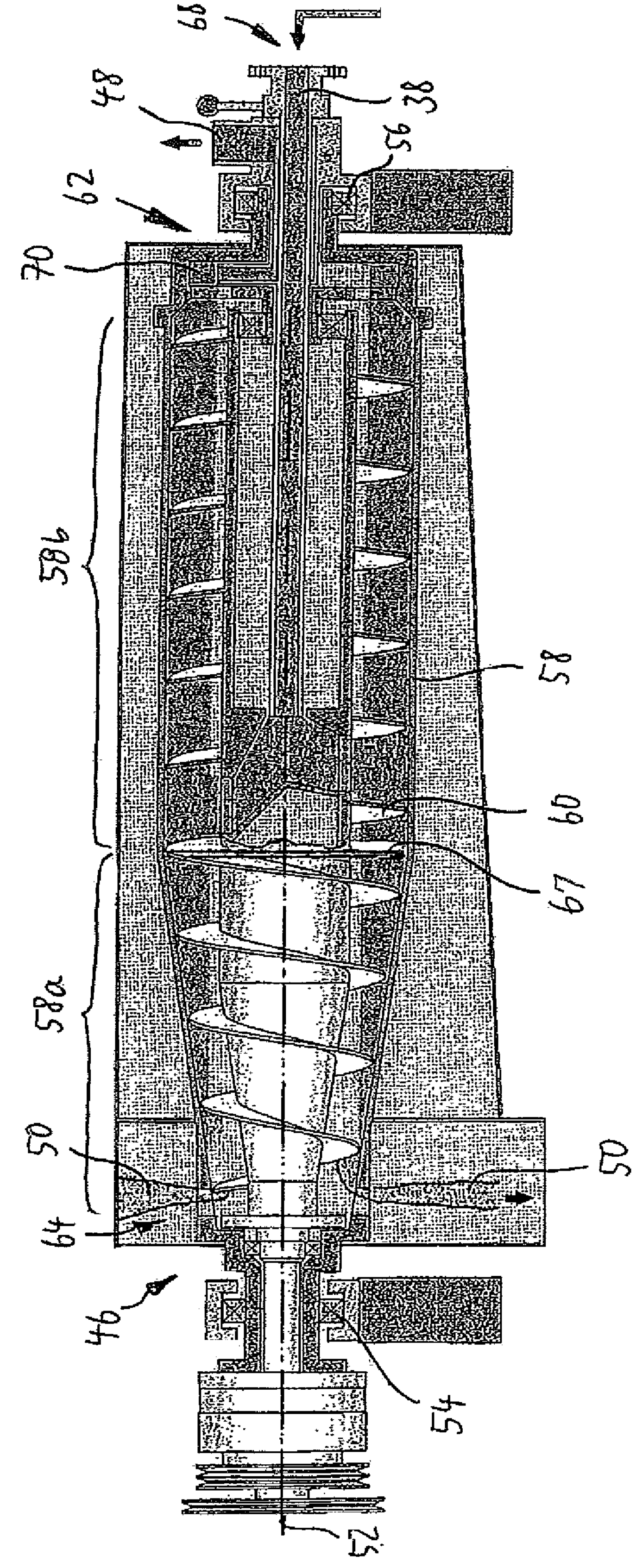
FIG. 7 is a longitudinal sectional view of a device similar to FIG. 6 modified according to the invention.

The syrup 38 to be separated in the horizontal axis centrifuge 46 is again conducted into the bowl 58 through an inlet 68. The recovered oil 48 is discharged under pressure via the first outlet 62 through the impeller disk 70, which may be adjusted even during rotation of bowl 58 and screw 60. The deoiled syrup 50 is again discharged via the screw 60 along said conical part 58*a* through the second outlet 64. For improvement of the process of discharging the deoiled syrup 50 relative to the recovered oil 48, FIG. 7 shows a modified horizontal axis centrifuge 46 in which a radial directed baffle plate 67 is located in one of the windings of screw 60 at the transition of the cylindrical part 58*b* of the bowl 58 and conical part 58*a*.

Figure 8:
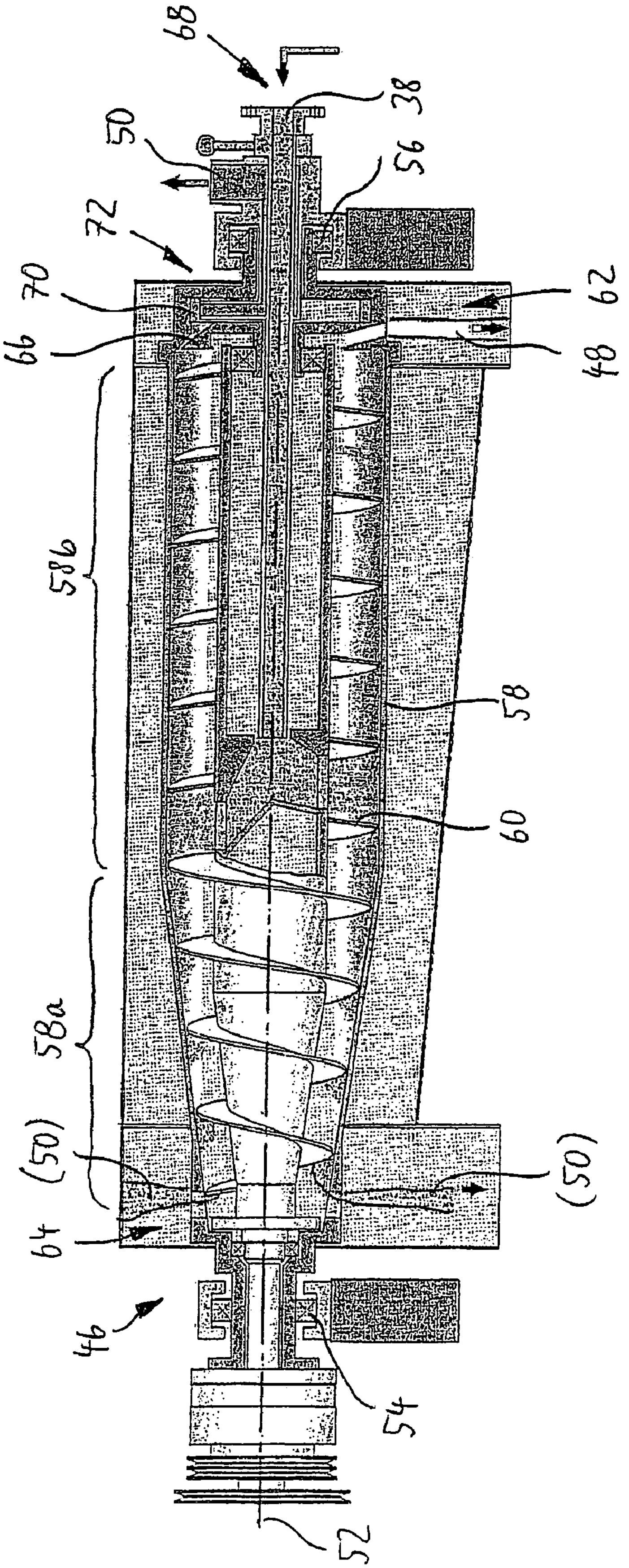
FIG. 8 is a longitudinal sectional view of a third embodiment of a device for increasing the yield of oil production in the process of producing bio-ethanol according to the invention.

FIG. 8 shows a third embodiment of a horizontal axis centrifuge 46 for the recovering of oil 48 according to the process of FIG. 3. The horizontal axis centrifuge 46 of FIG. 8 is a three-phase horizontal axis centrifuge also including a horizontal rotation axis 52 and two bearings 54 and 56 on which a rotatable drum or bowl 58 and a rotatable screw 60 are supported. The bowl 58 is provided with a first outlet 62 for a "first liquid phase", a second outlet 64 for a "solid phase", and a third outlet 72 for a "second liquid phase".

The syrup 38 to be separated in the horizontal axis centrifuge 46 is again conducted into the bowl 58 through an inlet 68.

The first outlet 62 is provided with an adjustable weir disk 66 and serves for discharging recovered oil 48.

The second outlet 64 is usually not used for discharging any material during the process of separating syrup 38. In contrast, the second outlet 64 serves for finally emptying the bowl 58 after the end of operation of the horizontal axis centrifuge 46. The screw 60 helps to spread the syrup 38 into the bowl 58 during the process of separation and to discharge residual material through the second outlet 64 at the end of the process.

The deoiled syrup 50 is discharged under pressure via the third outlet 72, which is provided with an adjustable impeller disk 70.

Alternatively, the second outlet 64 may serve for additionally discharging deoiled syrup 50 out of the bowl 58. Therefore, the deoiled syrup 50 is discharged via the screw 60 along the conical part 58*a*.

Figure 9:
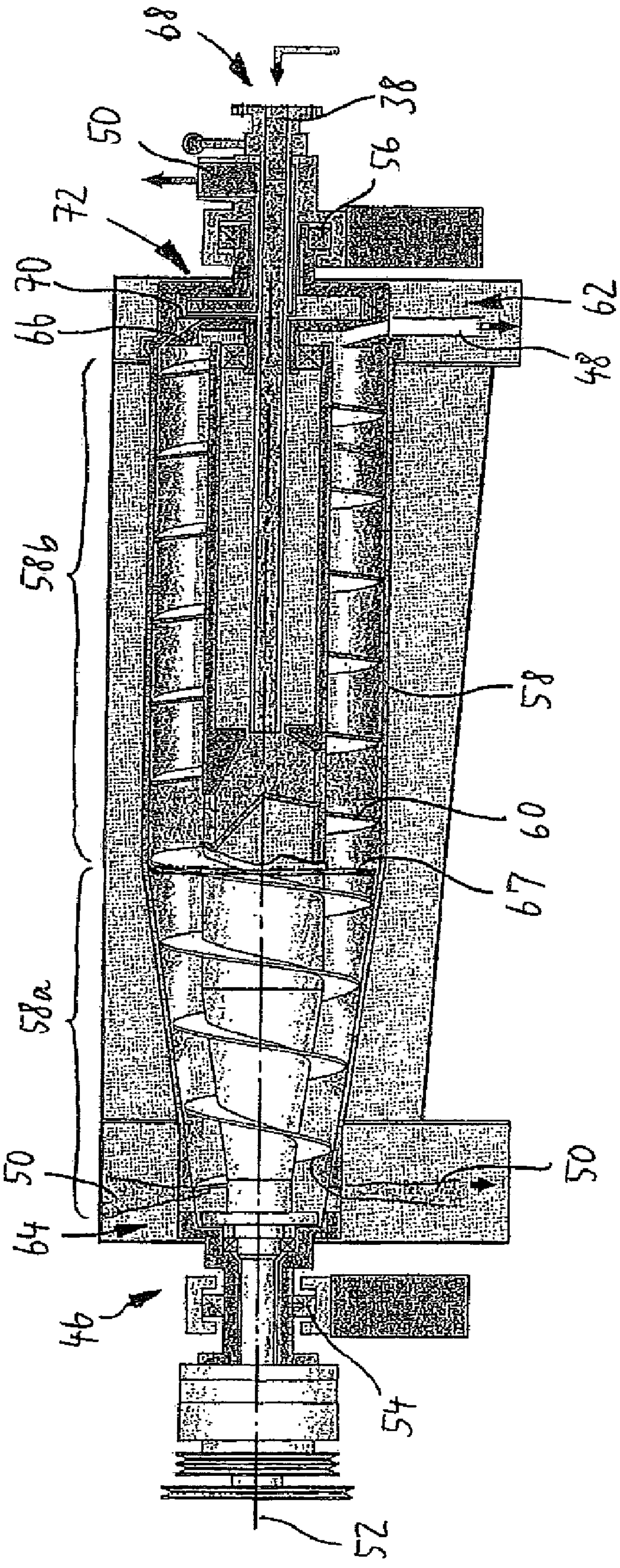
FIG. 9 is a longitudinal sectional view of a device similar to FIG. 8 modified according to the invention.

For further improving the process of discharging the deoiled syrup 50 through the second outlet 64 relative to the recovered oil 48, FIG. 9 shows a modified three-phase horizontal axis centrifuge 46 in which a radial directed baffle plate 67 is located in one of the windings of screw 60 at the transition of the cylindrical part 58*b* and conical part 58*a* of the bowl 58. The first outlet 62 thereby forms a discharge of oil the discharge diameter of which being 0.90 to 1.10 times of the respective diameter of a corresponding discharge of deoiled syrup.

Figure 10:
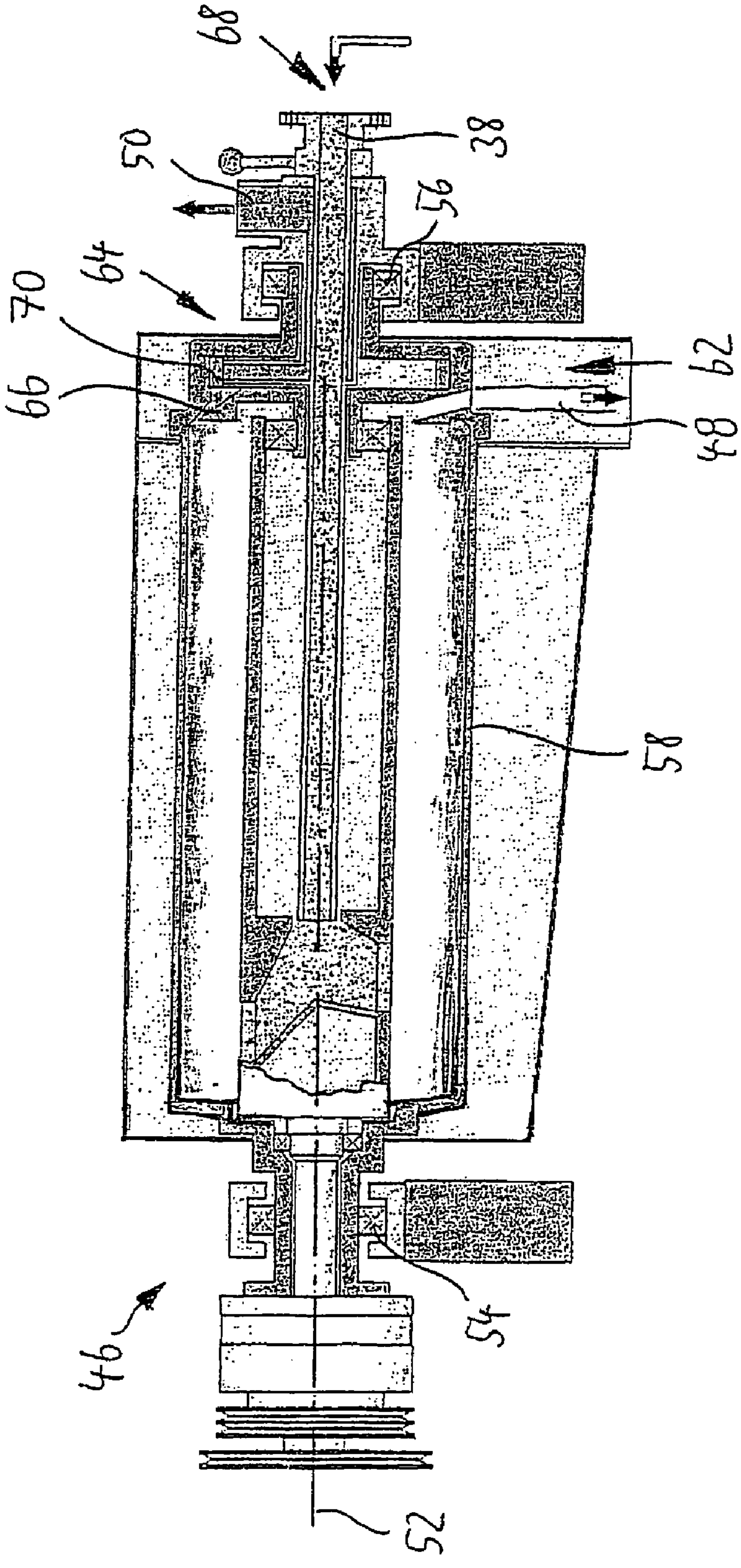
FIG. 10 is a longitudinal sectional view of a forth embodiment of a device for increasing the yield of oil production in the process of producing bio-ethanol according to the invention.

In FIG. 10 a fourth embodiment of a horizontal axis centrifuge 46 for the recovering of oil 48 according to the process of FIG. 3 is depicted. The horizontal axis centrifuge 46 of FIG. 10 is a two-phase horizontal axis centrifuge including a horizontal rotation axis 52 around which a rotatable drum or bowl 58 is located. The bowl 58 is provided with a first outlet 62 and a second outlet 64, both provided at one side wall of the bowl 58. Alternatively, the second outlet 64 may be provided at a side wall opposite to the one of the first outlet 62.

The syrup 38 to be separated in the horizontal axis centrifuge 46 of FIG. 10 is again conducted into the bowl 58 through an inlet 68.

The first outlet 62 is provided with an adjustable weir disk 66 and serves for discharging recovered oil 48.

The second outlet 64 includes an adjustable impeller disk 70 and serves for discharging deoiled syrup 50 under pressure.

Further, at the horizontal axis centrifuge 46 of FIG. 10 (non-depicted) means for finally cleaning and removing residual material out of the bowl 58 may be provided.

What is claimed is:

1. A method of increasing the yield of oil production in a process of producing bio-ethanol comprising: creating concentrated syrup as a by-product from an ethanol production, and recovering oil from the concentrated syrup, wherein the step of recovering oil from the concentrated syrup includes introducing the concentrated syrup to a horizontal axis centrifuge, using the horizontal axis centrifuge to recover oil, wherein the step of using the horizontal axis centrifuge comprises conducting the concentrated syrup into a bowl, separating the oil from the concentrated syrup using a screw and a baffle plate, wherein the step of using the screw and baffle plate includes discharging a recovered oil stream through a first outlet and discharging a deoiled syrup stream through a second outlet, wherein the step of using the baffle plate includes conveying deoiled syrup toward the second outlet and retaining oil at the baffle plate to prevent the oil from discharging at the second outlet.

2. The method of claim 1, wherein the step of using a screw and a baffle plate comprises using a baffle plate having a diameter which is 0.70 to 0.95 times diameter of the bowl of the horizontal axis centrifuge.

3. The method of claim 1, wherein the step of using a horizontal axis centrifuge includes discharging the recovered oil stream from the horizontal axis centrifuge using an adjustable weir disk.

4. The method of claim 1, wherein the step of using a horizontal axis centrifuge includes discharging the recovered oil stream from the horizontal axis centrifuge using an impeller disk.

5. The method of claim 1, wherein the step of creating concentrated syrup as a by-product from an ethanol production includes producing whole stillage, recovering thin stillage from the whole stillage by using a horizontal axis centrifuge and concentrating the thin stillage by using an evaporator.

6. The method of claim 1, wherein the step of recovering oil from the concentrated syrup includes storing the concentrated syrup in a storage tank before conducting it to the horizontal axis centrifuge.

7. The method of claim 6, wherein the step of conducting the concentrated syrup from the storage tank to the horizontal axis centrifuge includes drawing off the concentrated syrup at the top of the syrup stored in the storage tank.

8. The method of claim 1, wherein the step of using a horizontal axis centrifuge includes providing a centrifugal acceleration of 1800 to 2100×G on the concentrated syrup in the horizontal axis centrifuge.

9. The method of claim 1, wherein the diameter of the first outlet is 0.90 to 1.10 times the diameter of the second outlet.

10. The method of claim 1, wherein the step of creating concentrated syrup as a by-product from an ethanol production includes producing whole syrup, recovering thin syrup from the whole syrup by using a horizontal axis centrifuge and concentrating the thin syrup by using an evaporator.

11. The method of claim 1, wherein the step of using a horizontal axis centrifuge comprises using a three-phase horizontal axis centrifuge.

12. The method of claim 11, wherein the step of using a three-phase horizontal axis centrifuge includes discharging the recovered oil from the three-phase horizontal axis centrifuge using an adjustable weir disk.

13. The method of claim 11, wherein the step of using a three-phase horizontal axis centrifuge includes discharging the recovered oil from the three-phase horizontal axis centrifuge using an impeller disk.

14. The method of claim 11, wherein the step of creating concentrated syrup as a by-product from an ethanol production includes producing whole stillage, recovering thin stillage from the whole stillage using a three-phase horizontal axis centrifuge and concentrating the thin stillage using an evaporator.

15. The method of claim 11, wherein the step of recovering oil from the concentrated syrup includes storing the concentrated syrup in a storage tank before conducting it to a three-phase horizontal axis centrifuge.

16. The method of claim 15, wherein the step of conducting the concentrated syrup from the storage tank to a three-phase horizontal axis centrifuge includes drawing off the concentrated syrup at the top of the liquid stored in the storage tank.

17. The method of claim 11, wherein the step of using a three-phase horizontal axis centrifuge includes providing a centrifugal acceleration of 1800 to 2100×G on the concentrated syrup in the horizontal axis centrifuge.

18. The method of claim 1 wherein the step of using a horizontal axis centrifuge comprises using a baffle plate positioned between two windings of a screw positioned in a transition region between a cylindrical and conical section of a bowl.

19. The method of claim 18 wherein the step of using a horizontal axis centrifuge includes using a baffle plate which extends outward from a hub of a screw radially toward an interior wall of a bowl.

20. The method of claim 18 wherein the step of using a horizontal axis centrifuge includes using a baffle plate which extends outward from a hub of a screw orthogonal to a horizontal rotation axis.

* * * * *

US007915458C1

(12) EX PARTE REEXAMINATION CERTIFICATE (9441st)

United States Patent

Bruckmayer

(10) Number: US 7,915,458 C1

(45) Certificate Issued: Dec. 14, 2012

(54) METHOD OF AND DEVICE FOR INCREASING THE YIELD OF OIL PRODUCTION IN A PROCESS OF PRODUCING BIO-ETHANOL

(75) Inventor: Peter Bruckmayer, Velden-Eberspoint (DE)

(73) Assignee: Flottweg GmbH & Co. KGAA, Vilsbiburg (DE)

Reexamination Request:

No. 90/011,973, Nov. 11, 2011

Reexamination Certificate for:

| | |
|---|---|
| Patent No.: | **7,915,458** |
| Issued: | **Mar. 29, 2011** |
| Appl. No.: | **11/604,435** |
| Filed: | **Nov. 27, 2006** |

(51) Int. Cl.
*C07C 29/00* (2006.01)

(52) U.S. Cl. ........................................................ 568/840

(58) Field of Classification Search ........................ None
See application file for complete search history.

(56) References Cited

To view the complete listing of prior art documents cited during the proceeding for Reexamination Control Number 90/011,973, please refer to the USPTO's public Patent Application Information Retrieval (PAIR) system under the Display References tab.

*Primary Examiner* — Timothy J. Kugel

(57) ABSTRACT

A method of increasing the yield of oil production in a process of producing bio-ethanol in particularly comprises: creating concentrated syrup as a by-product from an ethanol production, and recovering oil from the concentrated syrup, wherein the step of recovering oil from the concentrated syrup includes using a horizontal axis centrifuge, and wherein the step of using a horizontal axis centrifuge includes using a bowl, a discharge of deoiled syrup and a baffle plate, the baffle plate being located inside of the bowl and retaining oil from the discharge of deoiled syrup.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 2, 4, 7, 10, 13, 16 and 18-20 is confirmed.

Claims 1, 3, 5, 6, 8, 9, 11, 12, 14, 15 and 17 are cancelled.

* * * * *